(12) United States Patent
Louw et al.

(10) Patent No.: US 9,310,330 B2
(45) Date of Patent: Apr. 12, 2016

(54) ELECTROCHEMICAL FLOW CELL

(71) Applicant: Antec Leyden B.V., Zoeterwoude (NL)

(72) Inventors: Herman Robert Louw, Alphen aan den Rijn (NL); Hendrik-Jan Brouwer, Leiderdorp (NL); Nicolaas Reinhoud, Woerden (NL)

(73) Assignee: ANTEC LEYDEN B.V., Zoeterwoude (NL)

( * ) Notice: Subject to any disclaimer, the term of this patent is extended or adjusted under 35 U.S.C. 154(b) by 498 days.

(21) Appl. No.: 13/650,468

(22) Filed: Oct. 12, 2012

(65) Prior Publication Data

US 2014/0102916 A1  Apr. 17, 2014

(51) Int. Cl.
*G01N 27/28* (2006.01)
*G01N 30/64* (2006.01)
*G01N 27/49* (2006.01)

(52) U.S. Cl.
CPC .............. *G01N 27/28* (2013.01); *G01N 27/49* (2013.01); *G01N 30/64* (2013.01); *G01N 2030/645* (2013.01)

(58) Field of Classification Search
CPC ........ G01N 27/28; G01N 27/49; G01N 30/64
See application file for complete search history.

(56) References Cited

U.S. PATENT DOCUMENTS 5,399,256 A * 3/1995 Bohs et al. .................... 204/409

* cited by examiner

*Primary Examiner* — Luan Van
*Assistant Examiner* — Gurpreet Kaur
(74) *Attorney, Agent, or Firm* — Young & Thompson (57) ABSTRACT

Described is an electrochemical flow cell (1) for analyzing fluid samples including a first member (100) including a first working surface (101), the first working surface (101) including a sample outlet (102), and a second member (200) including a second working surface (201), the second working surface (201) including a working electrode (202). The first and second member (100, 200) being connectable to each other to create a chamber (2) in between the first (101) and second working surface (201). The first working surface (101) being opposite and spaced apart from the second working surface (201) and the sample outlet (102) being directed at the working electrode (202). The electrochemical flow cell (1) includes an adjustment element for stepless adjustment of a distance (d) between the first working surface (101) and the second working surface (201).

22 Claims, 7 Drawing Sheets

ELECTROCHEMICAL FLOW CELL

TECHNICAL FIELD

The invention relates to an electrochemical flow cell.

STATE OF THE ART

Electrochemical flow cells are used in HPLC with electrochemical detection to analyze fluid samples to detect the presence and quantity of analytes contained in the sample. Electrochemical detection is used in many research fields, such as pharmaceutical and biotech applications, clinical and diagnostics applications, food analysis, etc. In the field of neuroscience electrochemical detection is used to measure neurotransmitters from particular brain regions. Concentrations are close to the detection limit of current analytical methods. The need for more time resolution in microdialysis experiments results in smaller sample volumes (<5 µL).

Ease of use, serviceability, linear dynamic range and robustness are key issues in daily use of electrochemical cells. Especially in trace analysis applications such as neurotransmitters there is a continuous need for electrochemical flow cells with improved performance in terms of signal-to-noise ratio.

Different flow cell concepts are known, such as thin-layer, porous flow through and wall-jet. Antec developed a wall-jet cell with an effective cell volume of 1-1000 nl, known as the VT-03. Thanks to this concept, the cell can be miniaturized and used in uLC without losing performance. It is well-known that microbore LC has less peak dilution, resulting more signal. Miniaturization using micro electrodes results in a low noise. So the combination results in an improved signal-to-noise ratio.

U.S. Pat. No. 5,399,256 describes an electrochemical detector cell which includes a first block having a planar first working surface, and a first working electrode embedded in the first block member. The first working electrode includes an analyte contacting surface disposed coplanarly with the first working surface.

A second block member has the second working surface placeable in an opposed, adjacent relation to the first working surface, and has an inlet port disposed in an opposed, adjacent relation to the analyte contacting surface of the first working electrode. The second block also includes coupling means for permitting an analyte delivery tube to be coupled to the second block member to position an end of the analyte delivery tube adjacent to the inlet port. A generally circular circumferential channel for collecting analyte is disposed radially outwardly of the first working electrode. An outlet is disposed at the channel for conducting analyte away from the channel. A reference electrode is disposed in a diametrically opposed relation to the outlet. A ring-like gasket is placeable between the first and second block members for maintaining the first and second working surfaces in a predetermined spaced relation. The gasket may be made from mylar, teflon, or polyethylene.

The gasket includes a radially inner diameter disposed radially outwardly of the channel. The inlet port, channel, first working electrode, first working surface, second working surface, gasket and outlet port are configured to create a generally centrosymmetric thin layer radial flow path for the analyte across the working electrode, and between the first and second working surfaces, into the channel and out of the outlet port.

According to U.S. Pat. No. 5,399,256, by changing the gasket thickness, the user can adjust the linear flow rate of the analyte across the working electrode at any given volume flow rate. The thicker the gasket, the slower the linear velocity of the analyte flowing across the working electrode surface.

The use of gaskets is cumbersome. In order to determine the optimal gasket thickness, for instance in search of an optimal signal-noise ratio, the electrochemical detector cell needs to be taken apart and re-assembled.

In Flow Characteristics of a Versatile Wall-Jet or Radial-Flow Thin-Layer Large-Volume Cell for Electrochemical Detection in Flow-Through Analytical Systems, by Benoît Soucaze-Guillous (Electroanalysis 1997, 9, No. 1, page 32-39), a large-volume flow-through cell is described comprising a micrometer screw for adjustment of a distance between the surface of the working electrode and the nozzle of the inlet capillary. However, the cell according to this article is complicated in use.

SHORT DESCRIPTION

It is an object of the invention to provide an improved electrochemical flow cell.

According to an aspect there is provided an electrochemical flow cell for analyzing fluid samples comprising a first member comprising a first working surface, the first working surface comprising a sample outlet, and a second member comprising a second working surface, the second working surface comprising a working electrode, the first and second member being connectable to each other to create a chamber in between the first and second working surface, the first working surface being opposite and spaced apart from the second working surface and the sample outlet being directed at the working electrode, characterized in that the electrochemical flow cell comprises adjustment means for stepless adjustment of a distance between the first working surface and the second working surface.

The distance between the first and second working surfaces may be such that a distance between the sample outlet and the working electrode may be in the range of 0-300 µm, for instance in the range 0-150 µm or 0-100 µm, resulting in excellent performance in ultra-trace analysis.

By providing adjustment means for stepless adjustment of the distance between the first and second working surfaces, the use of cumbersome spacers or gaskets is eliminated. Also, while adjustment involves movement of the entire first or second working surface, the shape of the first or second working surfaces is not changed as a result of the adjustment. So, the distance between the sample outlet and the working electrode may be done without changing the shape of the working surfaces, which make experimental results done with different distance comparable to each other.

The adjustment means may be arranged to adjust the position of the first working surface with respect to the first member. Alternatively the adjustment means may be arranged to adjust the position of the second working surface with respect to the second member.

The adjustment means allow to adjust the working volume of the electrochemical flow cell without opening the electrochemical flow cell. This allows for an easy optimization of the detection sensitivity for any LC application. Also, the stabilization time needed after changing the distance is strongly reduced, as the distance can now be changed without opening, reducing the chance of contaminating/destabilizing the chamber.

Also, by providing stepless adjustability, the distance (and thus the working volume) can be set at any desired distance within a predetermined range.

The working volume, i.e. the volume between the working electrode and the first working surface, may be varied in a stepless manner, for instance in a range of 0-2.5 µl to optimize the S/N ratio.

For instance, the working electrode may have a diameter of 2 mm, the distance between the two working surfaces may vary between 0-100 µm, resulting in a working volume between approximately 0-300 nl. According to an other example, the working electrode may have a diameter of 5 mm, the distance between the two working surfaces may vary between 0-100 µm, resulting in a working volume between approximately 0-2.5 µl.

The electrochemical flow cell may be in particular advantageous for (ultra) high performance liquid chromatography (U)HPLC with electrochemical detection (ECD) equipment.

According to an embodiment the electrochemical flow cell comprises an O-ring positioned in between the first and second working surface to seal the chamber along a perimeter of the chamber, the O-ring being flexible to follow the stepless adjustment of the distance between the sample outlet and the working electrode.

The O-ring is preferably made of flexible material, such as elastomers, silicones. According to an example, the O-ring is made of DuPont™ Kalrez® (perfluoroelastomer).

The O-ring is preferably flexible in an axial direction (with respect to the ring) to seal the chamber for all possible distances between the sample outlet and the working electrode which are settable by the adjustment means.

Preferably the O-ring is leak-free up to 25 bar, or even higher pressures. It is noted that an O-ring provides a much better sealing than for instance FEP gaskets which can thus withstand higher pressures. This is particular advantageous in combination with further downstream equipment, such as a mass spectrometer, which can result in a higher pressure inside the electrochemical flow cell.

The first or second working surface may comprise a circumferential wall only along its perimeter to keep the O-ring in position. The wall is thus only present along the outer perimeter of the O-ring. No wall or the like is provided against the inside of the O-ring, as this only reduces the available volume inside the chamber.

The O-ring is thus provided in a semi-groove, which is closed along the outer perimeter and is open towards the inside of the chamber. This has the advantage that no contamination can reside in such as poorly accessible and poorly flushed cavity, which could lead to corrosion/oxidation or unwanted contribution to backcurrent/noise or contamination of the mobile phase. Also, is it easier to clean such an electrochemical flow cell. According to an embodiment, the electrochemical flow cell has a pressure resistance of 20 bar or more.

According to an embodiment the first member and the second member comprise corresponding screw threads to connect the first housing to the second housing.

Such a design allows for easy manual assembly and disassembly of the electrochemical flow cell without the use of any mechanical tools. Maintenance and cleaning of the flow cell is thus easy and can be done in a time-efficient way. Also, such an electrochemical cell allows to quickly change the first and second members if needed.

According to an embodiment the adjustment means are formed by the corresponding screw threads which enable adjusting the distance between the first and second housing with respect to each other.

By simply rotating the first and second housings with respect to each other, the distance between the first and second working surface can be adjusted. The outside of the housing may comprise marks to indicate the distance, allowing a user to set a desired distance in an easy way.

According to an embodiment the first or second member comprises a housing and a working surface member accommodated in the housing, the working surface member comprising the first or second working surface, wherein the adjustment means are provided to adjust the relative position of the first or second working surface with respect to the housing.

According to an embodiment the first or second member comprises:
a housing comprising an inner screw thread defining a body axis,
a rotatable member comprising an outer screw thread which engages with the inner screw thread of the housing, the rotatable member further comprising an inner screw thread, and
a working surface member comprising the first or second working surface, the working surface member comprising an outer screw thread which engages with the inner screw thread of the rotatable member,
wherein the outer screw thread of the rotatable member is oppositely wound with respect to the inner screw thread of the rotatable member,
wherein the working surface member is rotatably fixed with respect to the housing and the working surface member can slide with respect to the housing in a direction of the body axis upon rotation of the rotatable member.

This is an advantageous embodiment, as it provides accurate and simple adjustment means by means of rotation, without rotating the first and second working surfaces with respect to each other. This makes it easier to seal the chamber along its perimeter. In particular in case the chamber is sealed with an O-ring, it is advantageous to be able to adjust the height of the first and second working surface without rotating them with respect to each other, as rotation could cause deformation of the O-ring.

Furthermore, because of the double screw threads, accurate adjustment means are provided. Rotation of the rotatable member will result in opposite movement of the rotatable member and the working surface member with respect to the housing, which results in accurate adjustment means.

According to an example, the displacement of this mechanism may be 250 µm/360°.

Threaded connections may suffer from play in between the two engaging threads. Especially play in a direction parallel to the body axis, i.e. the direction in which the distance between the sample outlet and the working electrode can be set, could have a negative effect on the accuracy in which the distance between these two elements can be set. Adjusting the distance may suffer from hysteresis.

So, according to an embodiment the first or second member comprises a pre-stressing element provided in between the housing and the rotatable member to apply a pre-stressing force in a direction parallel to the body axis.

Play and hysteresis are reduced by this embodiment, as the pre-stressing element provides a pre-stressing force in the direction of the body axis. The pre-stressing element may be a spring, such as a cup spring or spring disc.

The housing may comprise an inwardly protruding rim, whereby the rim faces a surface of the rotatable member perpendicular to the body axis, whereby the pre-stressing element is provided in between the rim and the surface of the rotatable member. Also, the pre-stressing element generates friction between corresponding screw parts, reducing the chance of unwanted to apply enough force/friction to prevent the rotatable member from rotating freely (resulting in unwanted changes of the working volume).

The pre-stressing force is preferably a repulsive force, forcing the rotatable member away from each other.

According to an embodiment the electrochemical flow cell comprise one or more stop members to limit the stepless adjustment of the distance (d) to a minimum and/or maximum distance.

Providing a stop member to limit the adjustment to a pre-fixed range (for example 0-100 μm) is advantageous, as a minimum distance prevents the working electrode and the sample outlet being pushed together with too much force, resulting in damaging. Providing a stop member to limit the adjustment to a maximum distance prevents the distance from becoming too large, which could result in leakage of the chamber and also prevents disassembly of the adjusting mechanism.

According to an embodiment the electrochemical flow cell comprises a cover member arranged to receive the first or second member and engage with the other of the first and second member to position and hold the first and second member with respect to each other.

This result in a compact electrochemical flow cell which can be assembled in an easy and fast way, without the need of assembly tools or spacers/gaskets. This also makes maintenance easy and fast and allows for quickly changing one of the first or second members.

According to an embodiment the housing of the other of the first and second member comprises an outer screw thread and the cover member comprises an inner screw thread or vice versa which engage with each other.

Preferably, the first or second member can rotate inside the cover member (rotation about an axis parallel to the rotational axis of the screw threads and parallel to a direction perpendicular to the surface of the working electrode). This allows to assemble and disassemble the electrochemical flow cell without rotating the first and second member with respect to each other. Such mutual rotation is cumbersome as the first and second members may be connected to electrical equipment and/or fluid conduits. Such rotation may also damage the O-ring.

According to an embodiment the second working surface comprises a central, circular surface portion comprising the working electrode in a central position thereof, the second working surface further comprising a ring shaped channel surrounding the circular surface portion.

This configuration ensures that a uniform and stable flow pattern is created. The sample outlet is preferably directed perpendicular to the centre of the working electrode, resulting in a radial flow pattern away from the centre of the working electrode towards the channel.

According to an embodiment the electrochemical flow cell has a working volume ($V_{working}$) equal to the surface area of the working electrode multiplied by the distance between the first and second working surface, and the electrochemical flow cell has a total volume ($V_{total}$) in between the first and the second working surface, wherein $V_{total} \gg V_{working}$, preferably $V_{total} > 50 * V_{working}$. The working volume $V_{working}$ for this embodiment is the working volume determined for a predetermined distance between the working electrode and the sample outlet of 100 μm. In a practical embodiment the following relation may apply: $V_{total} > 1000 * V_{working}$.

By providing a relatively large total volume, it has been found that the quality of the measurement results is improved. The working volume ($V_{working}$) is defined as the surface area of the working electrode multiplied by the distance between the first and second working surface at the position of the working electrode.

The large total volume may be accomplished by creating a large channel. For instance, the channel may have a curvature with a radius which is at greater than 0.75 times the radius of the central, circular surface portion. The chamber may have an outer diameter which is greater than 3 times diameter of the central, circular surface portion.

According to an embodiment the second surface portion has a curved, ring-shaped convex transition portion in between the elevated surface portion and the ring shaped channel.

This specific shape contributes to a smooth, steady flow pattern, which increases the quality of the measurements. The convex transition portion may have a curvature of 0.5 mm.

According to an embodiment the first member comprises a first working surface which comprises a sample outlet connectable to a sample tube to receive a sample fluid. The sample fluid is introduced into the chamber via the sample outlet. The sample outlet may also be referred to as a nozzle. The first member comprises a sample supply channel.

According to an embodiment the first or second member further comprises a sample discharge channel for discharging sample fluid from the chamber.

The sample discharge channel may run from the first or second working surface to a top surface of the first member or bottom surface of the second member and may be connected to a waste tube to guide the sample fluid to a waste.

According to an embodiment the second working surface comprises a central, circular surface portion comprising a bore in a central position thereof in which the working electrode is pressed, the central circular surface portion and the working electrode forming a flat surface.

The working electrode and the central circular surface portion 220 may be flat and may have a roughness Ra<0.5 μm. Preferably, the entire first and/or second working surface has a roughness of Ra<0.5 μm. A roughness of Ra<0.5 μm contributes to a smooth and steady flow pattern in the chamber 2 which is beneficial for the signal-to-noise ratio of the measurements.

According to an embodiment the first member further comprises a reference electrode connection, connectable to a reference electrode.

The reference electrode connection may be a socket or the like, arranged to receive a plug to which a reference voltage can be applied. The reference electrode connection may be in electrical connection with the chamber such that in use, it is in electrical connection with the sample fluid.

According to an embodiment the second member comprises an auxiliary electrode socket, to connect the second working surface to an auxiliary electrode.

It will be understood that the second working surface is connectable to an auxiliary electrode, but that this doesn't include the working electrode.

The auxiliary electrode socket may be positioned in a bottom surface of the second member in the rotatable member at a position remote from the centre such that the auxiliary electrode socket may be engaged by a tool to rotate the rotatable member.

According to an aspect there is provided a detection system for analyzing fluid sample, comprising a separation system for separating different analytes from the fluid sample and an electrochemical flow cell according to any one of the preceding claims, wherein the electrochemical flow cell is controlled by an electrochemical detector or potentiostat and the electrochemical flow cell is connected to the separation system to detect the separated analytes from the separation system.

The separation system may be a chromatographic separation system, downstream of the electrochemical flow cell a further measurement device is provided, such as a mass spectrometer.

According to an aspect there is provided a method of analyzing a fluid sample comprising:
 a) providing a detection system as defined above,
 b) analyzing the fluid sample using the detection system.

According to an embodiment the method comprises repeating the following actions in between action a) and b):
 performing test measurements,
 determining a signal-to-noise ratio of the calibration measurements,
 adjusting a distance between the first working surface and the second working surface of the electrochemical flow cell, and
 determining an optimal distance with an optimal signal-to-noise ratio and setting the distance to the optimal distance.

Adjusting the distance is done without opening the electrochemical flow cell.

According to an embodiment determining an optimal distance comprises interpolation between distances at which test measurements were performed.

According to an embodiment analyzing the fluid sample comprises introducing the fluid sample into the chamber and creating a pressure of 20 bar or more inside the chamber.

Such a pressure is not a goal but a result of the coupling the electrochemical flow cell to downstream equipment. So, according to an embodiment, the electrochemical flow cell has a pressure resistance of 20 bar or more. This is advantageous to ensure that enough pressure can built up in the electrochemical flow cell for further downstream equipment, such as a mass spectrometer.

This is also advantageous in UHPLC applications in which relatively high flow rations and thus pressures are used.

SHORT DESCRIPTION OF THE DRAWINGS

Embodiments will now be described, by way of example only, with reference to the accompanying schematic drawings in which corresponding reference symbols indicate corresponding parts, and in which.

DETAILED DESCRIPTION

Figure 1A:
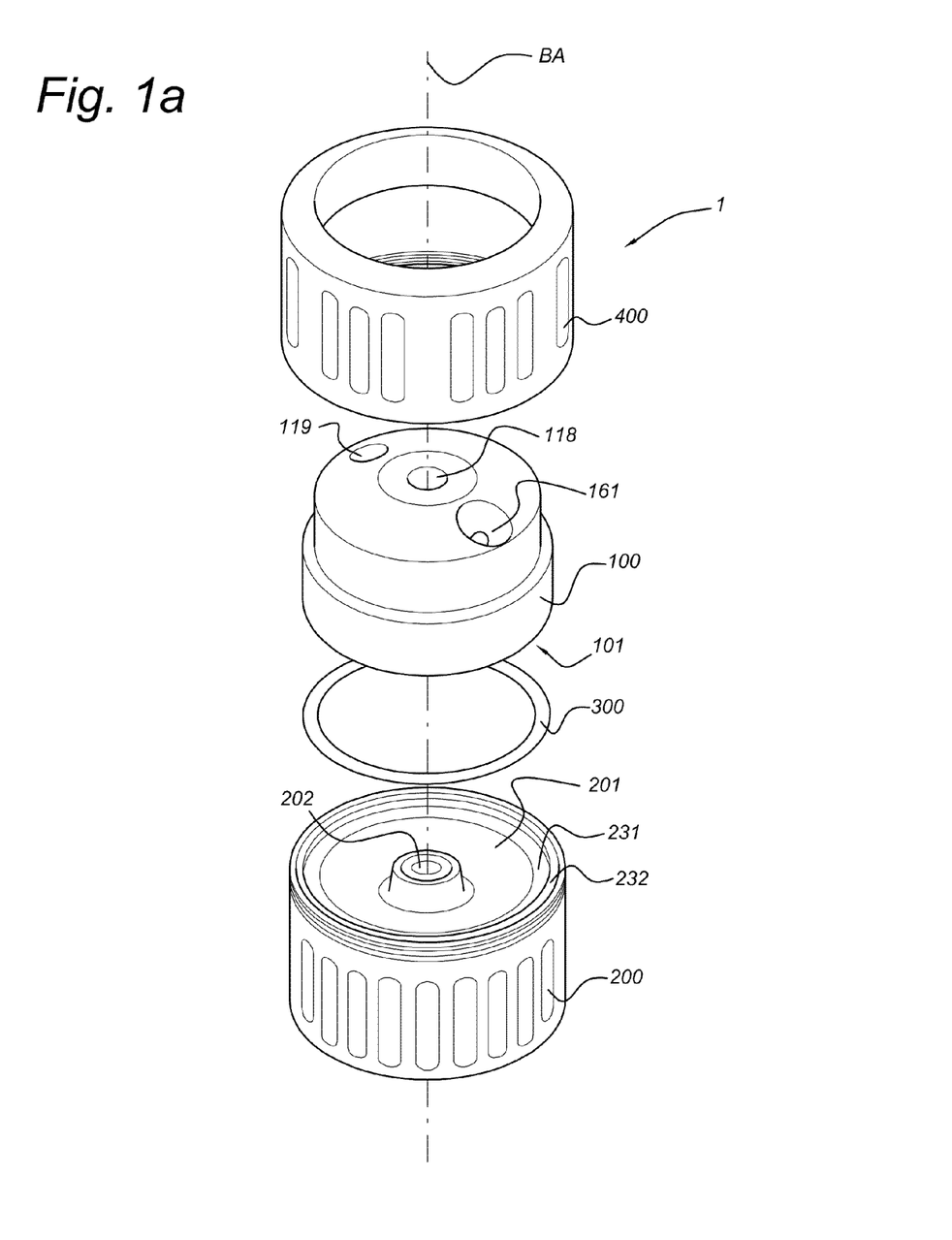
FIGS. 1*a* and 1*b* schematically depicts an electrochemical flow cell according to an embodiment in disassembled and assembled state respectively, FIG. 2*a* schematically depicts a top view of an electrochemical flow cell according to an embodiment.
Figure 1B:
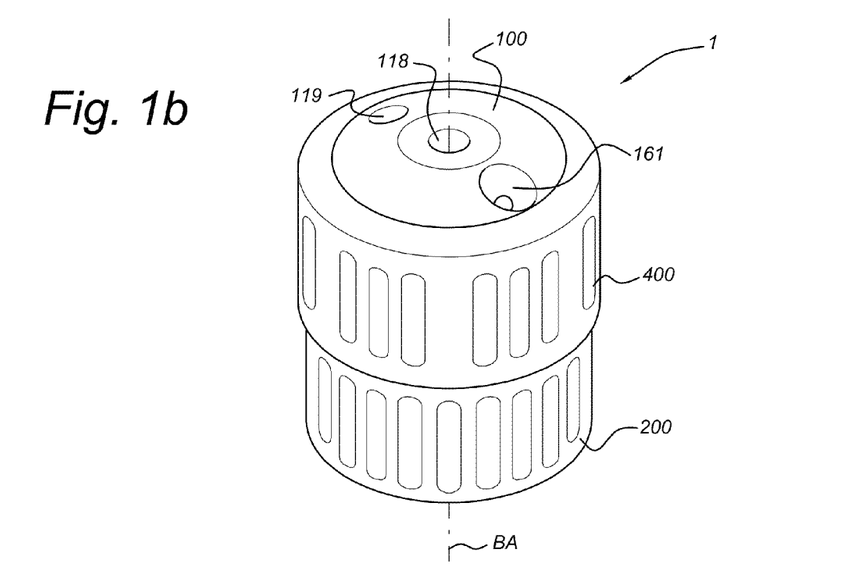

FIG. 1*a* shows an electrochemical flow cell 1 according to an embodiment in disassembled state, comprising a first member 100, a second member 200, an O-ring 300 and a cover member 400. FIG. 1*b* shows these elements in assembled state. The first member 100 is positioned inside the cover member 400. The cover member 400 engages with the second member 200 by means of corresponding screw threads, clamping the first and second member 100, 200 on top of each other and the O-ring 300 in between the first and second member 100, 200. FIGS. 1*a* and 1*b* also show body axis BA.

Figure 2A:
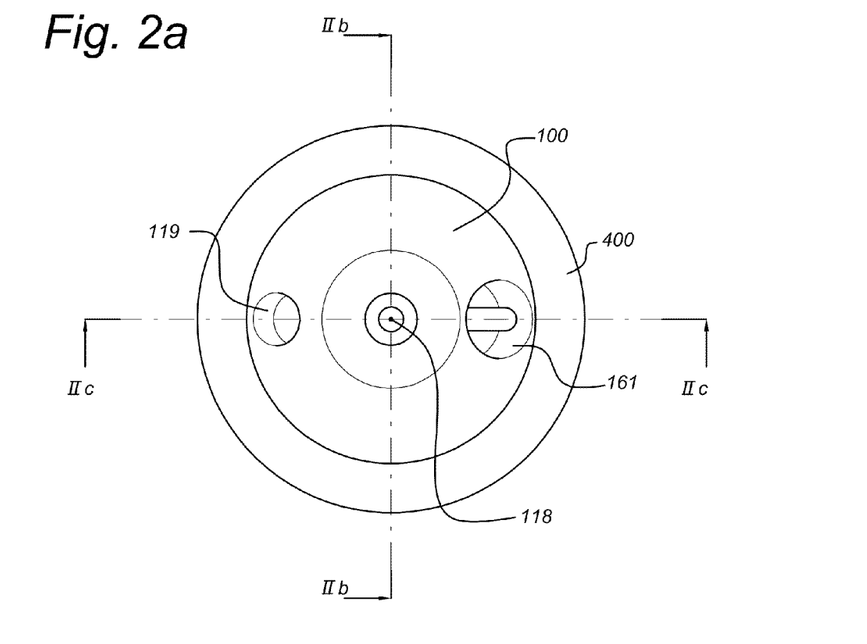
Figure 2B:
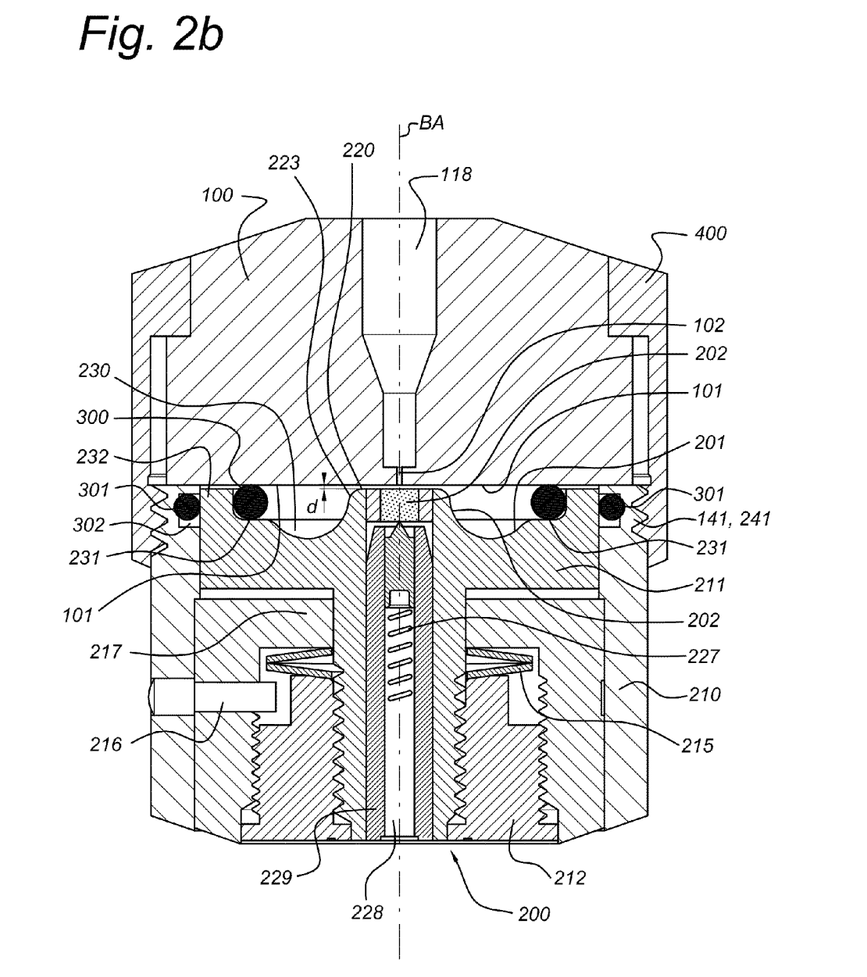
FIGS. 2*b* and 2*c* show cross-sectional views of the electrochemical flow cell according to FIG. 2*a*, FIGS. 3 and 4 show a cross-sectional view of an electrochemical flow cell according to different embodiments.
Figure 2C:
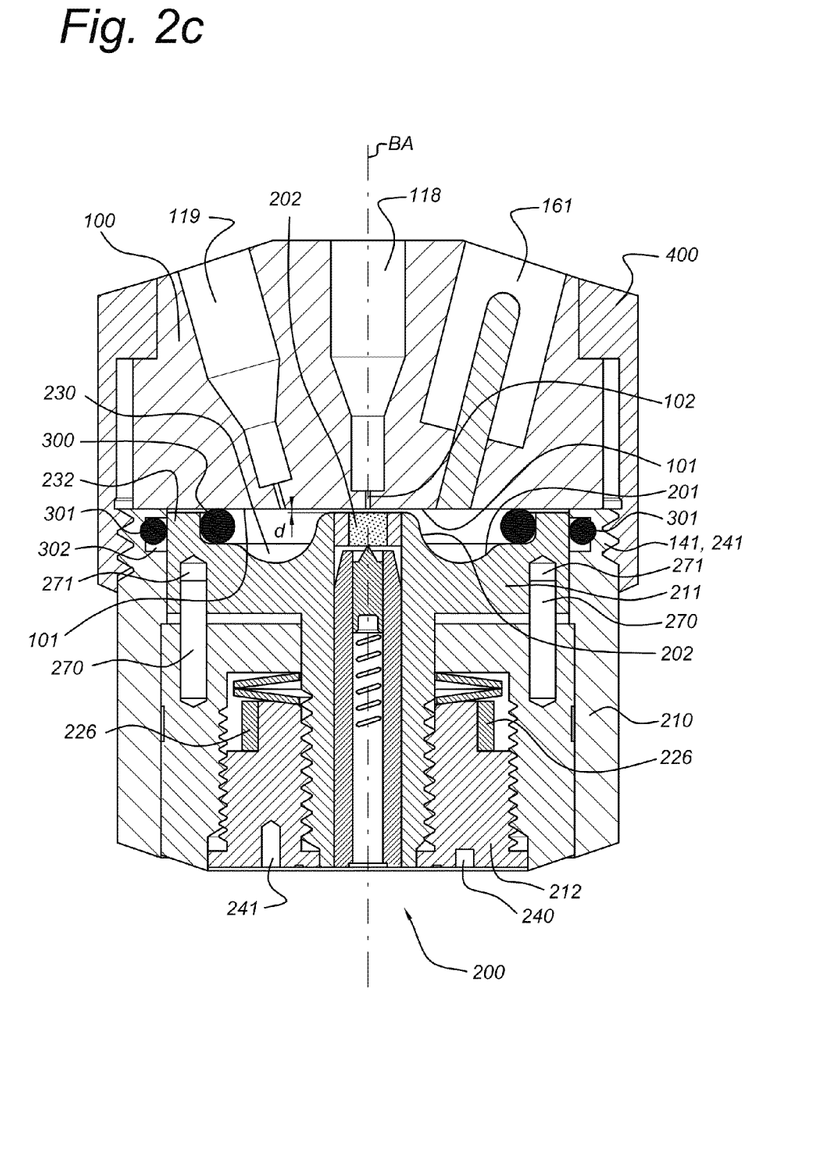

FIG. 2*a* shows a top view of the electrochemical flow cell in assembled state. FIGS. 2*b* and 2*c* show cross sectional views of the electrochemical flow cell in assembled state as indicated in FIG. 2*a*.

The first member 100 as shown comprises a sample supply channel 118, a sample discharge channel 119 and, optionally a reference electrode connection 161.

The second member 200 comprises a working electrode 202 which is connectable to a working electrode terminal via socket 288. The socket 228 is isolated by a isolated sleeve 229 surrounding the socket 228. Inside the socket 228 is a spring member 227 to guarantee adequate electrical connection.

FIGS. 2*b* and 2*c* show that the first member 100 comprises a first working surface 101, which comprises the sample outlet 102 of the sample supply channel 118. The second member 200 comprises a second working surface 201 with the working electrode 202. In between the first and second working surface 101, 201 a chamber 2 is created.

The sample outlet 102 and the working electrode 202 are positioned opposite each other such that the sample fluid introduced via the sample outlet 102 hits the working electrode 202 perpendicular and flows away from the working electrode 202 radially.

The second member 200 also comprises an auxiliary electrode socket 240, to connect the second working surface to an auxiliary electrode, i.e. part of the second working surface not comprising and being electrically isolated from the working electrode 202.

The auxiliary electrode socket 240 may be positioned in a bottom surface of the second member in the rotatable member at a position remote from the centre such that the auxiliary electrode socket 240 may be engaged by a tool to rotate the rotatable member as will be explained in more detail below. For this purpose, a further socket 241 may be provided to facilitate rotation. This further socket 241 has no electrical function.

The auxiliary electrode may be a plug which is inserted in the auxiliary electrode socket 240 which is electrically connected to the metal part/stainless steel part of the second working surface 201 surrounding the working electrode 201 and bine isolated from the working electrode 201.

The first member 100 comprises reference electrode connection 161, connectable to a reference electrode which in use is in contact with the sample fluid inside the chamber 2 to provide stable circumstances during measurements.

The functioning of the electrochemical flow cell will be known by a skilled person and is therefore only briefly explained.

The electrochemical flow cell 1 is in use controlled by a electrochemical detector or potentiostat. The electrochemical flow cell 1 is connected to an upstream separation system, such as a chromatographic separation system, for separating different analytes from the fluid sample and receives a sample fluid into the sample supply channel 118 and introduces the fluid samples into the chamber 2.

A working potential is set between the working electrode 202 and the auxiliary socket 240 by means of an auxiliary electrode. The auxiliary electrode is kept at a precisely defined reference electrode (REF) potential by means of a so-called voltage clamp. This is an electronic feedback circuit that compensates for polarisation effects at the electrodes.

Different references electrodes may be used, such as a Ag/AgCl saltbridge, Pd/H2 (HyREF) and the ISAAC (In-Situ Ag/AgCl) REF. The reference electrodes can be changed quickly and easy in the embodiments described here.

As shown in FIGS. 2b and 2c, the second working surface 201 comprises a central, circular surface portion 220 comprising the working electrode 202. A channel 230 is provided around the central, circular surface portion 220. The channel 230 has a radial outer portion 231, preferably flat, to support the O-ring 300. Along the outer perimeter of the radial outer portion 231 a circumferential wall is provided to keep the O-ring in position.

In use, at the working electrode 202, which is kept at virtual ground, the electrochemical reaction (oxidation or reduction) takes place, i.e. electrons are transferred at the working electrode 202. This results in an electrical current to an I/E converter, which is a special type of operational amplifier. The output voltage can be measured by an integrator or recorder and provides information about the contents of the sample.

FIG. 2b shows that the second member 200 comprises adjustment means for stepless adjusting a distance between the first working surface and the second working surface. The distance may for instance be measured between the sample outlet 102 and the working electrode 202.

The second member 200 comprises a housing 210 and a working surface member 211 accommodated in the housing 210. The housing 210 is formed as a sleeve and is hollow to receive other parts of the second member 200, such as the working surface member 211 which comprises the second working surface 201. The adjustment means are provided to adjust the relative position of the second working surface 201 with respect to the housing 210. The housing 210 comprises an inner screw thread defining a body axis. Concentrically inside the housing 210, in between the housing 210 and the working surface member 211 is a rotatable member 212, which is formed as a sleeve with an outer and inner screw thread, the inner screw thread being oppositely wound with respect to the outer screw thread. The inner screw thread and the outer screw thread engage with an outer screw thread of the working surface member 211 and an inner screw thread of the housing 210 respectively.

The working surface member 211 is rotatably fixed to the housing 210, as shown in FIG. 2c, by means of protrusions 270 (e.g. pins) in the direction of the body axis BA from the housing 210 and corresponding recesses 271 formed in the working surface member 211 to receive the protrusions 270 which prevent rotation of the working surface member 211 with respect to the housing 210, but allow movement of the working surface member 211 with respect to the housing 210 in the direction of the body axis BA upon rotation of the rotatable member 211 about the body axis BA. The body axis BA is preferable perpendicular to the surface of the working electrode 202. The rotatable member 212 is also capable of moving with respect to the housing 210 and the working surface member 211 in the direction of the body axis BA and is also capable of rotating about the body axis BA with respect to the housing 210 and the working surface member 211.

An annular chamber 302 may be present between the housing 210 and the working surface member 211 in which a second O-ring 301 is provided to facilitate movement of the housing 210 and the working surface member 211 with respect to each other. Also, this annular chamber 302 is for sealing off the internal cell parts from liquid/fluid which could lead to corrosion or other problems.

In between an inward protrusion 217 of the housing 210 and the rotatable member 211 a spring is provided which applies a pre-stressing force in a direction parallel to the body axis BA between the housing and the rotatable member 211.

The electrochemical flow cell 1 comprises one or more stop members 217 to limit the stepless adjustment of the distance to a minimum and maximum distance. In FIG. 2b one stop member 216 is shown. The top part of the rotatable member 211 is not circular but has an increased diameter and/or height over a predetermined part of its circumference (as shown in FIG. 2c by element 226) such that rotational movement of the rotational member 211 is limited. Of course, more than one stop member or a differently shaped top part of the rotatable member 212 may be provided.

As shown in FIGS. 1a-2c, a cover member 400 is provided arranged to receive the first member 100 and which engages with the second member 200 to position and clamp the first and second member 100, 200 with respect to each other. The second member 200 and the cover member 400 may have corresponding screw threads 141, 241 which engage each other in assembled state.

Figure 3:
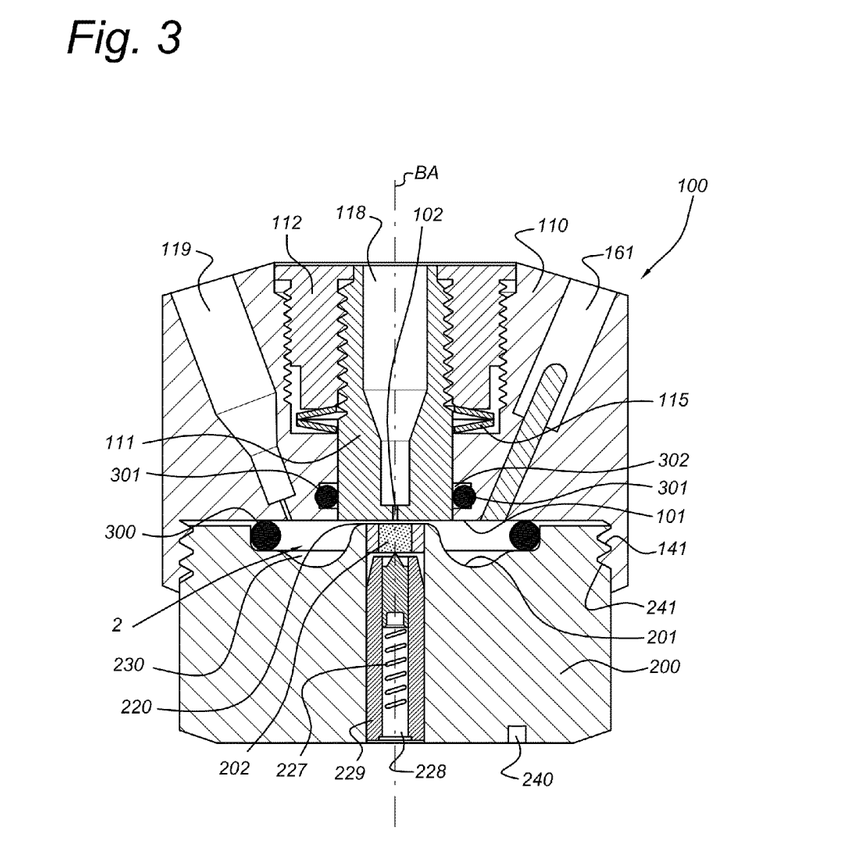

FIG. 3 shows an alternative embodiment in which the adjustment means are provided in the first member 100 and the cover member 400 is arranged to receive the second member 200 and which engages with the first member 100 to position and clamp the first and second member 100, 200 with respect to each other. According to this embodiment, the first member 100 comprises a housing 110 and a working surface member 111 accommodated in the housing 110. The housing 110 is formed as a sleeve and is hollow to receive other parts of the second member 100, such as the working surface member 111 which comprises the first working surface 101. The adjustment means are provided to adjust the relative position of the first working surface 101 with respect to the housing 110. The housing 110 comprises an inner screw thread defining a body axis (BA). Concentrically inside the housing 110, in between the housing 110 and the working surface member 111 is a rotatable member 112, which is formed as a sleeve with an outer and inner screw thread, the inner screw thread being oppositely wound with respect to the outer screw thread. The inner screw thread and the outer screw thread engage with an outer screw thread of the working surface member 111 and an inner screw thread of the housing 110 respectively. According to the embodiment shown in FIG. 3, the first member 100 also functions as cover member 400. However, a separate cover member 400 may be provided similar to the embodiment shown in FIG. 2a-2c.

Figure 4:
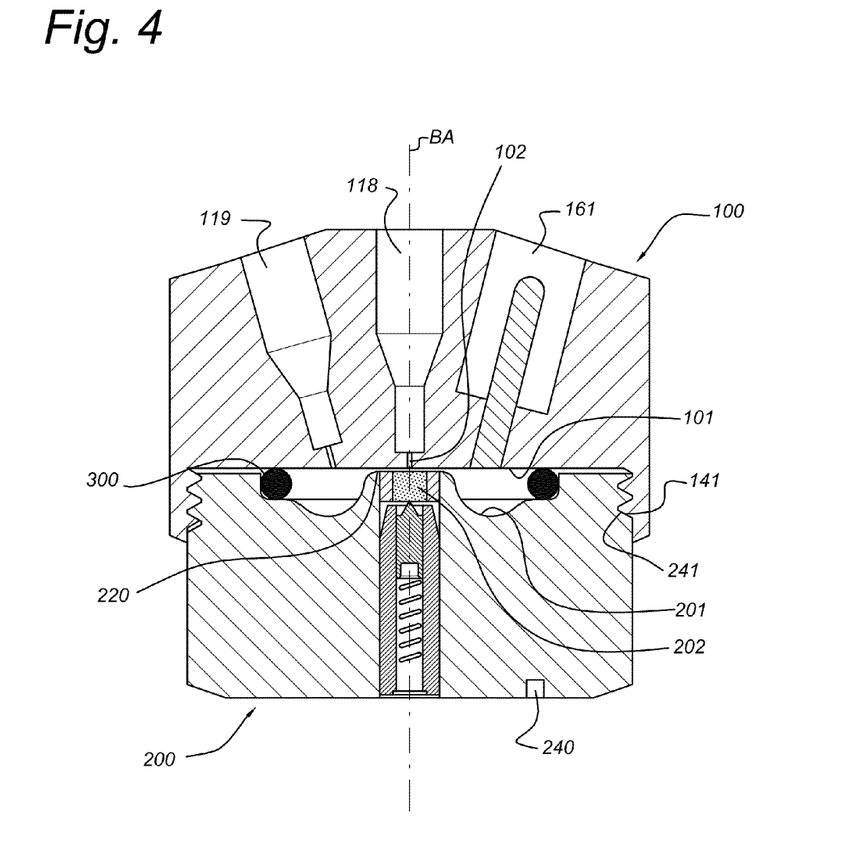

FIG. 4 shows yet a further embodiment in which the first and second members 100, 200 are directly coupled by means of corresponding screw threads, which also function as adjustment means to stepless adjust the distance between the first and second working surface.

EXPERIMENTS

The performance of an electrochemical flow cell as described was evaluated over its usable working volume range. The usable working volume range is defined by the lower limit where noise excessively increases, and the upper limit which is the max setting. The working volume was varied to approximately 30-300 nL corresponding to a spacing distance of 10-100 µm. Samples of 1.5 µL of a 100 nM standard of Dopamine in 10 mM HAc were injected. The electrochemical flow cell used for this experiment comprised a Glassy Carbon working electrode (WE) and both signal and noise were evaluated. The results are shown in FIG. 5a.

Figure 5A:
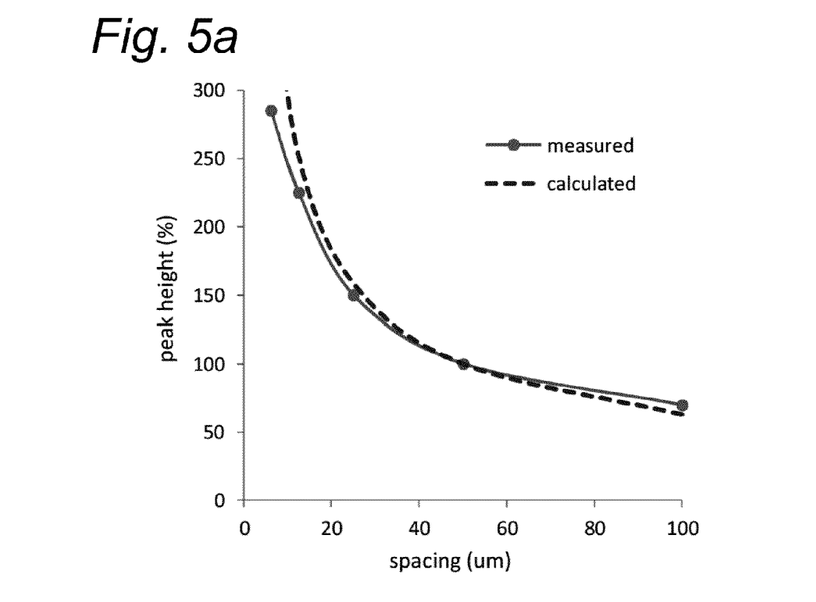
FIG. 5*a*-5*b* show test results.

The relative response (peak height) is plotted in FIG. 5a. Over the usable working range a relative increase of over a factor 3 in signal was observed for the flow cell under test.

This was in correspondence with theoretical calculations based on the Cotrell equation. (Lit ref F. G. Cottrell, Z. Phys. Chem 42 (1903) 385)

Figure 5B:
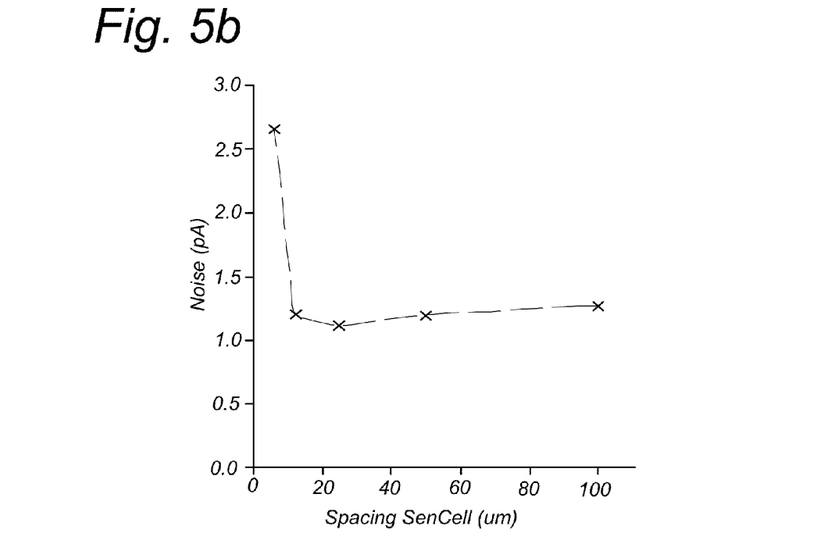

The noise was relatively constant over the usable working volume range, which shows that an increase in signal-to-noise ratio of a factor three is achievable. This is shown in FIG. 5b.

So, the electrochemical flow cell according to the embodiments has an optimized wall-jet design and shows improvements in signal-to-noise characteristics which makes the cell suitable for ultra-trace analysis of for example neurotransmitters in dialysates and brain homogenates.

Of course, it is understood that the electrochemical flow cell 1 may be used in a wide range of applications, such as neuroscience, clinical diagnostics, environmental, food, pharmaceutics etc.

The descriptions above are intended to be illustrative, not limiting. Thus, it will be apparent to one skilled in the art that modifications may be made to the invention as described without departing from the scope of the claims set out below.

The invention claimed is:

1. Electrochemical flow cell for analyzing fluid samples comprising:
    a first member comprising a first working surface, the first working surface comprising a sample outlet,
    a second member comprising a second working surface, the second working surface comprising a working electrode,
    the first and second member being connectable to each other to create a chamber in between the first and second working surface, the first working surface being opposite and spaced apart from the second working surface and the sample outlet being directed at the working electrode, and
    adjustment means for stepless adjustment of a distance (d) between the first working surface and the second working surface,
    wherein the first or second member comprises:
    a housing comprising an inner screw thread defining a body axis (BA),
    a rotatable member comprising an outer screw thread which engages with the inner screw thread of the housing, the rotatable member further comprising an inner screw thread, and
    a working surface member comprising the first or second working surface, the working surface member comprising an outer screw thread which engages with the inner screw thread of the rotatable member,
    wherein the outer screw thread of the rotatable member is oppositely wound with respect to the inner screw thread of the rotatable member, and
    wherein the working surface member is rotatably fixed with respect to the housing and the working surface member can slide with respect to the housing in a direction of the body axis (BA) upon rotation of the rotatable member.

2. Electrochemical flow cell according to claim 1, wherein the electrochemical flow cell comprises an o-ring positioned in between the first and second working surface to seal the chamber along a perimeter of the chamber the O-ring being flexible to follow the stepless adjustment of the distance between the sample outlet and the working electrode.

3. Electrochemical flow cell according to claim 1, wherein the first member and the second member comprise corresponding screw threads to connect the first member to the second member.

4. Electrochemical flow cell according to claim 3, wherein the adjustment means are formed by the corresponding screw threads which enable adjusting the distance between the first and second members with respect to each other.

5. Electrochemical flow cell according to claim 1, wherein the adjustment means are provided to adjust the relative position of the first or second working surface with respect to the housing.

6. Electrochemical flow cell according to claim 1, wherein the first or second member comprises a pre-stressing element provided in between the housing and the rotatable member to apply a pre-stressing force in a direction parallel to the body axis (BA).

7. Electrochemical flow cell according to claim 1, wherein the electrochemical flow cell comprise one or more stop members to limit the stepless adjustment of the distance (d) to a minimum and maximum distance.

8. Electrochemical flow cell according to claim 1, wherein the electrochemical flow cell comprises a cover member arranged to receive one of the first member and second member and engage with one of the first member and second member to position and hold the first and second member with respect to each other.

9. Electrochemical flow cell according to claim 8, wherein the housing of the one of the member first and second members engaged with the cover member comprises an outer screw thread and the cover member comprises an inner screw thread or vice versa which engage with each other.

10. Electrochemical flow cell according to claim 1, wherein the second working surface comprises a central, circular surface portion comprising the working electrode in a central position thereof, the second working surface further comprising a ring shaped channel surrounding the circular surface portion.

11. Electrochemical flow cell according to claim 1, wherein the electrochemical flow cell has a working volume equal to the surface area of the working electrode multiplied by the distance between the first and second working surface, and the electrochemical flow cell has a total volume in between the first and the second working surface, wherein $V_{total} \gg V_{working}$, preferably $V_{total} > 50 * V_{working}$ 12. Electrochemical flow cell according to claim 10, wherein the second surface portion has a curved, ring-shaped convex transition portion in between an he elevated surface portion and the ring shaped channel.

13. Electrochemical flow cell according to claim 1, wherein the first member comprises a first working surface which comprises a sample outlet connectable to a sample tube to receive a sample fluid.

14. Electrochemical flow cell according to claim 1, wherein the first or second member further comprises a sample discharge channel for discharging sample fluid from the chamber.

15. Electrochemical flow cell according to claim 1, wherein the second working surface comprises a central, circular surface portion comprising a bore in a central position thereof in which the working electrode is pressed, the central circular surface portion and the working electrode forming a flat surface.

16. Electrochemical flow cell according to claim 1, wherein the first member further comprises a reference electrode connection connectable to a reference electrode.

17. Electrochemical flow cell according to claim 1, wherein the second member comprises an auxiliary electrode socket to connect the second working surface to an auxiliary electrode.

18. Detection system for analyzing fluid sample, comprising a separation system for separating different analytes from the fluid sample and an electrochemical flow cell according to claim 1, wherein the electrochemical flow cell is controlled by an electrochemical detector or potentiostat and the electrochemical flow cell is connected to the separation system to detect the separated analytes from the separation system.

19. Method of analyzing a fluid sample comprising:
a) providing a detection system for analyzing a fluid sample, the detection system comprising
   a separation system for separating different analytes from the fluid sample and an electrochemical flow cell, wherein the electrochemical flow cell is controlled by an electrochemical detector or potentiostat and the electrochemical flow cell is connected to the separation system to detect the separated analytes from the separation system; and
   wherein the electrochemical flow cell comprises a first member comprising a first working surface, the first working surface comprising a sample outlet, a second member comprising a second working surface with a working electrode, the first and second member being connectable to each other to create a chamber in between the first and second working surface, the first working surface being opposite and spaced apart from the second working surface and the sample outlet being directed at the working electrode, and adjustment means for stepless adjustment of a distance between the first working surface and the second working surface, wherein the first or second member comprises:
   a housing comprising an inner screw thread defining a body axis (BA),
   a rotatable member comprising an outer screw thread which engages with the inner screw thread of the housing, the rotatable member further comprising an inner screw thread, and
   a working surface member comprising the first or second working surface, the working surface member comprising an outer screw thread which engages with the inner screw thread of the rotatable member,
   wherein the outer screw thread of the rotatable member is oppositely wound with respect to the inner screw thread of the rotatable member, and
   wherein the working surface member is rotatably fixed with respect to the housing and the working surface member can slide with respect to the housing in a direction of the body axis (BA) upon rotation of the rotatable member; and
b) analyzing the fluid sample using the detection system.

20. Method according to claim 19, wherein the method further comprises repeating the following actions in between action a) and b):
performing test measurements,
determining a signal-to-noise ratio of calibration measurements,
adjusting a distance between the first working surface and the second working surface of the electrochemical flow cell, and
determining an optimal distance with an optimal signal-to-noise ratio and setting the distance to the optimal distance.

21. Method according to claim 20 wherein determining an optimal distance comprises interpolation between distances at which test measurements were performed.

22. Method according to claim 19, wherein analyzing the fluid sample comprises introducing the fluid sample into the chamber and creating a pressure of 20 bar or more inside the chamber.

* * * * *